United States Patent [19]

Kawamata et al.

[11] 4,361,709

[45] Nov. 30, 1982

[54] PROCESS FOR THE PRODUCTION OF O-ALKYLATED PHENOLS

[75] Inventors: Motoo Kawamata; Kazushi Ohshima; Mitsuo Onofusa; Akihide Kudoh; Makoto Kotani, all of Yokohama; Takeshi Tsuda, Kanagawa, all of Japan

[73] Assignee: Mitsui Toatsu Chemicals, Inc., Tokyo, Japan

[21] Appl. No.: 265,600

[22] Filed: May 20, 1981

[30] Foreign Application Priority Data

Dec. 1, 1978 [JP] Japan .................................. 53-147764

[51] Int. Cl.$^3$ .............................................. C07C 37/11
[52] U.S. Cl. .................................... 568/804; 568/743; 568/794
[58] Field of Search ........................ 568/794, 804, 743; 252/471

[56] References Cited

U.S. PATENT DOCUMENTS

| | | | |
|---|---|---|---|
| 2,448,942 | 9/1948 | Winkler et al. | 568/794 |
| 2,713,037 | 7/1955 | Kimberlin | 252/453 |
| 3,446,856 | 5/1969 | Hamilton | 568/794 |
| 3,873,628 | 3/1975 | Van Sorge | 568/804 |
| 3,953,529 | 4/1976 | Yonomitsu et al. | 568/804 |
| 3,971,832 | 7/1976 | Watanabe et al. | 568/804 |
| 3,974,229 | 8/1976 | Pecak | 568/804 |
| 4,097,411 | 6/1978 | Van Sorge | 568/794 |
| 4,227,023 | 10/1980 | Kawamata et al. | 568/804 |

*Primary Examiner*—Werren B. Lone
*Attorney, Agent, or Firm*—Fisher, Christen & Sabol

[57] ABSTRACT

A process for the production of alkyl phenols having at least one o-alkyl radical comprising catalytically reacting a phenolic compound having at least one o-positioned hydrogen atom with an alcohol in the vapor phase in the presence of a manganese oxide containing catalyst modified with a compound of at least one of the alkali metals.

12 Claims, No Drawings

PROCESS FOR THE PRODUCTION OF O-ALKYLATED PHENOLS

BACKGROUND OF THE INVENTION

1. Field of the Invention

This invention relates to an improved process for producing o-alkylated phenols.

2. Description of the Prior Art

The synthesis of 2,6-dimethylphenol (2,6-xylenol), among other o-alkylated phenols, has heretofore been the subject of many studies, because it is useful as a raw material for the manufacturing of polyphenylene ethers having a wide range of utilities in the fields of synthetic resins.

Currently, a process for the ortho-alkylation of phenols is in industrial use. It involves the vapor phase reaction of a phenol with an alcohol in the presence of a solid acid catalyst such as alumina (refer to U.S. Pat. No. 2,713,037). However, in this process, the selectivity for the ortho-alkylation is insufficient. That is, the meta and para positions of the phenol as well as the ortho positions thereof are alkylated to a considerable extent, so that a complicated procedure for the separation and purification of the ortho-alkylated product is required.

Another industrial process is based on the use of a magnesium oxide catalyst (refer to U.S. Pat. Nos. 2,448,942 and 3,446,856). But, this catalyst has inherently low activity, so it requires reaction temperatures higher than 475° C., practically higher than 500° C., to perform the reaction sufficiently. Moreover, the life of the catalyst is not long enough, so the regeneration procedure must be required in a relatively short period of time for practical use.

In order to solve these problems, there have been proposed many kinds of catalysts, for example, those comprising various combinations of magnesium oxide and other oxides (refer to U.S. Pat. No. 4,097,411), those comprising various combinations of iron oxide and other components (refer to U.S. Pat. No. 3,953,529).

These catalysts, however, still have similar disadvantages mentioned above, partly they are insufficient in selectivity for ortho-alkylation and in service life and partly they induce the alkylation of undesired positions (other than the ortho positions) and the formation of polyalkylated products under such reaction conditions as to produce a satisfactorily high catalytic activity.

Meanwhile, a process for the selective ortho-alkylation of a phenolic compound having at least one ortho-positioned hydrogen atom by using a manganese oxide catalyst is disclosed in U.S. Pat. No. 3,971,832. The invention disclosed therein relates to a process for the ortho-methylation of a phenol which comprises contacting the vaporized phenol with an alcohol at a temperature of from 250° C. to 500° C. in the presence of a catalyst consisting essentially of trimanganese tetroxide previously calcined at a temperature of from 950° C. to 1,500° C. It is stated that one feature of the invention is to provide a process for the ortho-methylation of phenols with a very high degree of selectivity under mild reaction conditions. However, this process cannot succeed to provide sufficiently high degrees of conversion of the phenol and selectivity for o-cresol or 2,6-xylenol.

The present inventors made extensive studies on a catalyst system comprising manganese oxide as the major component, and have proposed a catalyst which is effective on a selective ortho-alkylation of phenols (refer to U.S. Pat. No. 4,227,023). However, in order to produce o-alkylated phenols advantageously on an industrial scale, it is necessary to reduce the accumulation rate of the hydrocarbon deposition on the surface of the catalyst, to further prolong the regeneration cycle of the catalyst, and consequently to prolong the catalyst life.

SUMMARY OF THE INVENTION

It is an object of this invention to provide an improved process for producing o-alkylated phenols by alkylating phenols on at least one of the ortho-positions.

It is another object of this invention to provide a process for producing o-alkylated phenols in which the regeneration cycle of the catalyst and the catalyst life can be prolonged.

The aforesaid objects of this invention can be attained by the use of a manganese oxide containing catalyst modified with a compound of at least one of the alkali metals.

According to this invention, the use of the manganese oxide containing catalyst makes it possible to suppress unnecessary decomposition of an alcohol during reaction, and consequently to decrease the accumulation rate of hydrocarbons on the surface of the catalyst resulting in a prolonged regeneration cycle of the catalyst and a prolonged catalyst life.

DETAILED DESCRIPTION OF THE INVENTION

Phenols used in the present invention are phenol compounds having a hydrogen atom on at least one of the ortho-positions thereof, and are represented by the general formula (I):

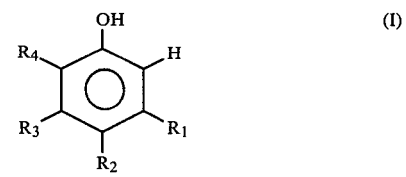

where $R_1$, $R_2$, $R_3$, and $R_4$ represent hydrogen, alkyl radicals of 1 to 4 carbon atoms, or unsubstituted or substituted phenyl radicals. Examples of the phenol usable in the present invention include phenol; phenols substituted with methyl radical such as o-, m-, or p-cresol, 2,3-, 2,4-, 3,4- or 3,5- xylenol, 2,3,4-, 2,3,5-, 2,4,5- or 3,4,5- trimethyl phenol, tetramethyl phenol, and the like; phenols substituted with other alkyl radicals in place of methyl radical such as ethyl phenols, n-, iso-, or tert- butyl phenol, and the like; phenyl phenol and the like, and many include phenol compounds substituted with at least one of different functional groups on the aromatic ring, preferably including phenol, o-, m-, or p-cresol, and 2,3-, 2,4-, 3,4- or 3,5- xylenol, more preferably phenol, and o-, m-, p- cresol.

Alcohols used in the present invention are saturated lower aliphatic alcohols, for example, methanol, ethanol, n-propanol, iso-propanol, n-butanol, iso-butanol, and tert-butanol, preferably methanol and ethanol, more preferably methanol.

A catalyst used in the present invention is a manganese oxide containing catalyst prepared by modifying a catalyst composition comprising manganese oxide and silicon oxide, or a catalyst composition further comprising at least one selected from alkaline earth metal oxides in addition thereto with a compound of at least one of the alkali metals.

In the case where alkaline earth metal is contained, the composition of the catalyst used in the present invention is such that an atomic ratio of Mn:Si:alkaline earth metal:alkali metal is generally in the range of from 100:0.01–20:0.01–30:10$^{-5}$–5, preferably 100:0.05–10:0.01–20:10$^{-4}$–1.

In the case where alkaline earth metal is not contained, an atomic ratio of Mn:Si:alkali metal is generally in the range of from 100:0.01–20:10$^{-5}$–5, preferably 100:0.05–10:10$^{-4}$–1. When the proportion of alkali metal therein is increased above the aforesaid range, both selectivity to ortho-position and temperature activity are reduced.

In the preparation of the manganese oxide containing catalyst modified with alkali metal, as the starting materials of manganese, silicon, alkaline earth metal and alkali metal, the hydroxides, the oxides, the halides, the carbonates, the mineral acid salts, the organic acid salts, and the like of respective metals can be used.

Examples of alkali metal compounds include hydroxides, oxides, halides, carbonates, mineral acid salts, and organic acid salts thereof, preferably hydroxides, oxides, and carbonates of sodium, potassium, rubidium, or cesium.

A number of methods are available for the preparation of the catalyst. For example, it may be prepared either by adding a small amount of water to a mixture of various compounds as described above and blending the mixture well in a kneader or mixer, or by adding a suitable precipitating agent to an aqueous solution of various compounds and separating the coprecipitated insoluble product. It is also possible to form a mixed oxide of manganese and silicon, or manganese, silicon and at least one of alkaline earth metals from suitable compounds at first, and then add an alkali metal compound thereto. Usually, the resulting catalyst is dried at a temperature below 200° C. calcined at a temperature of from 300° to 900° C. (which step may be omitted if desired), and then shaped by any conventional method to form a catalyst ready for use. Alternatively, it may be coated on a suitable carrier such as alumina, silica, steatite, carborundum, or the like and then calcined.

In carrying out the process of the invention, a phenolic compound and an alcohol are mixed in a molar ratio ranging from 1:1 to 1:14 and preferably from 1:1 to 1:8. Prior to feeding the reactants to the reaction zone, these starting materials may be diluted with a suitable inert gas such as nitrogen or carbon dioxide to make the reaction proceed smoothly. Furthermore, it is also effective to introduce a small amount of water with the reactants into the reaction zone. The presence of such water serves not only to prolong the service life of the catalyst but also to suppress any undesirable decomposition of the alcohol. The amount of water to be incorporated is such that a molar ratio of water based on alcohols as the starting material is in the range of from 1:0.01 to 1:1.

The process of the invention is carried out at a temperature of from 300° to 500° C. and preferably from 320° to 470° C. If the reaction temperature is higher, the selectivity for ortho-alkylation is reduced and the formation of various high-boiling products is increased. On the other hand, if the reaction temperature is lower, the conversion of the reactants is insufficient for the practical use, as a result, great amounts of unreacted starting materials or intermediate products must be recovered and recycled.

The reactants are preferably fed to the reaction zone at a liquid hourly space velocity (LHSV) of from 0.1 to 5 hr.$^{-1}$. Generally speaking, greater space velocities are suitably used for the reactions of higher temperature, and vice versa. The reaction may be carried out under a pressure higher or lower than atmospheric pressure. The reaction may be carried out according to any of the fixed bed, fluidized bed, and moving bed processes.

The present invention is further illustrated by the following examples.

EXAMPLE 1

1000 g of manganese nitrate 6-hydrate was dissolved in water at 40° C., and a solution prepared by diluting 20 g of sodium silicate (JIS-No. 3) with 100 ml of deionized water was added drop by drop to the above manganese solution. The aforesaid silicon containing manganese nitrate solution was diluted with 8 l of deionized water, and about 10% ammonia water was added thereto to pH 9 so that coprecipitates of manganese and silicon may be obtained.

To the coprecipitates, 0.2 g of cesium nitrate was added with thorough agitation, washed with water filtered, and dried with hot-air at 190° C. for 10 hours.

The resulting solid product was pulverized, molded to tablets of 4.8 mm$\phi \times$ 3 mm$\Sigma$ by a tablet machine, and then calcined at 500° C. for 10 hours to prepare a manganese oxide containing catalyst.

Then, 100 ml of this catalyst was packed into a stainless steel tubular reactor having an internal diameter of 25 mm and heated to 425° C. Thereafter, a mixture of phenol and methanol (a molar ratio of 1:5) was vaporized at 270° C., and then introduced into the reactor at a rate of 60 g per hour.

The reaction product was cooled by a water-cooled condenser and then collected in a dry ice-acetone trap. The product thus obtained was analyzed by g.l.c. After 5 hours' reaction, the conversion of phenol was 100%, the selectivities to o-cresol and 2,6-xylenol were 2.4% and 95.3% respectively, and after 100 hours' reaction, the conversion of phenol was 99.7%, the selectivities to o-cresol and 2,6-xylenol were 5.6% and 92.4% respectively.

EXAMPLES 2–6 AND CONTROL 1

Catalysts having various compositions were prepared in the same manner as described in Example 1. The results after 100 hours' reaction are summarized in Table 1.

TABLE 1

| Example | Catalyst Composition (atomic ratio) Mn:Si:Alkali metal | Reaction Temperature (°C.) | Conversion of Phenol (%) | Selectivity (%) o-Cresol | 2,6-xylenol |
|---|---|---|---|---|---|
| 2 | 100:2:0.1 (K) | 430 | 99.5 | 7.3 | 91.1 |
| 3 | 100:2:0.1 (Rb) | 425 | 99.7 | 5.9 | 92.7 |
| 4 | 100:2:1 (K) | 435 | 99.0 | 8.8 | 90.0 |
| 5 | 100:4:0.05 (Na) | 435 | 97.6 | 10.2 | 87.4 |
| 6 | 100:4:0.01 (Cs) | 430 | 99.4 | 5.3 | 93.0 |
| Control 1 | 100:2:0 | 440 | 91.2 | 19.3 | 73.1 |

EXAMPLE 7

1000 g of manganese nitrate 6-hydrate was dissolved in water at 40° C., and a solution prepared by diluting 20 g of sodium silicate (JIS-No. 3) with 100 ml of deionized water was added drop by drop to the above manganese solution. The aforesaid silicon containing manganese nitrate solution was diluted with 8 l of deionized water, and about 10% ammonia water was added thereto to pH9 so that coprecipitates of manganese and silicon may be obtained.

To the coprecipitates, 5 g of calcium hydroxide and 0.1 g of rubidium nitrate were added thereto with through agitation, washed with water, filtered, and dried with hot-air at 190° C. for 10 hours.

The resulting solid product was molded to tablets in the same manner as in Example 1, and calcined at 500° C. for 10 hours.

Then, 100 ml of this catalyst was packed into the reactor as described Example 1 and heated to 420° C. Thereafter, a mixture of phenol and methanol (a molar ratio of 1:7) was vaporized at 270° C., and then introduced into the reactor at a rate of 70 g per hour.

After 100 hour's reaction, the conversion of phenol was 99.9% and the selectivities to o-cresol and 2,6-xylenol were 3.3% and 93.7 respectively.

EXAMPLES 8-10

Catalysts having various compositions were prepared in the same manner as described in Example 1. The results after 100 hours' reaction are summarized in Table 2.

TABLE 2

| Example | Catalyst Composition (atomic ratio) Mn:Si:Alkaline earth metal:Alkali metal | Reaction Temperature (°C.) | Conversion of phenol (%) | Selectivity (%) o-cresol | 2,6-xylenol |
|---|---|---|---|---|---|
| 8 | 100:1.5:0.3(Sr):0.001(Cs) | 430 | 99.0 | 7.4 | 90.9 |
| 9 | 100:1:1(Ca):0.001(K) | 435 | 98.3 | 10.7 | 87.5 |
| 10 | 100:1:0.2(Mg):0.001(K) | 435 | 97.5 | 12.6 | 85.3 |

EXAMPLE 11

In the same procedure as in Example 1, ethanol was used instead of using methanol for carrying out the reaction. The conversion of phenol was 71.4%, and the selectivities to o-ethyl phenol and 2,6-diethyl phenol were 64.3% and 28.1% respectively.

EXAMPLES 12

In the same procedure as in Example 1, m-cresol is used instead of using phenol for carrying out the reaction.

The conversion of m-cresol was 100%, and the selectivities to 2,3- and 2,5- xylenols, and 2,3,6-trimethyl phenol were 3.2%, 1.1%, and 93.8% respectively.

What is claimed is:

1. In a process for producing an o-alkylated phenol wherein a phenol compound of the formula:

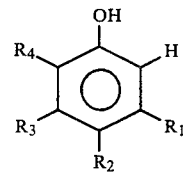

where $R_1$, $R_2$, $R_3$ and $R_4$ stand for hydrogen, alkyl radicals of 1 to 4 carbon atoms, or unsubstituted or substituted phenyl radicals, is reacted with a saturated aliphatic alcohol having from 1 to 4 carbon atoms in the presence of a catalyst at a temperature of from 300° to 500° C., the molar ratio of said phenol compound to said alcohol ranging from 1:1 to 1:15, the improvement in which said catalyst is selected from manganese oxide-containing catalysts prepared by modifying:
   (a) a catalyst composition comprising manganese oxide and silicon oxide, or
   (b) a catalyst composition comprising manganese oxide, silicon oxide and at least one alkaline earth metal oxide with at least one alkali metal compound, the atomic ratio of Mn:Si:alkali metal in said catalyst prepared by modifying the catalyst composition (a) being $100:0.01-20:10^{-5}-5$, and the atomic ratio of Mn:Si:alkaline earth metal:alkali metal in said catalyst prepared by modifying the catalyst composition (b) being $100:0.01-20:0.01-30:10^{-5}-5$.

2. A process as claimed in claim 1, wherein said alkali metal compound is selected from hydroxides, oxides, halides, carbonates, mineral acid salts, and organic acid salts.

3. The process of claim 1 wherein said alcohol is methanol.

4. The process of claim 3 wherein said phenol is phenol or a phenol substituted with at least one methyl radical.

5. The process of claim 1 wherein said phenol is selected from the group consisting of phenol, o-, m-, or p-cresol, 2,3-, 2,4-, 3,4- or 3,5-xylenol, 2,3,4-, 2,3,5-, 2,4,5- or 3,4,5-trimethyl phenol, and tetramethyl phenol, ethyl phenols, n-, iso-, or butyl phenols, phenyl phenol, and phenols substituted with at least one of o-, m-, or p-cresyl groups and 2,3-, 2,4-, 3,4- or 3,5-xylyl groups.

6. The process of claim 1 wherein said temperature is from 320° C. to 470° C.

7. A process as claimed in claim 1 wherein a small amount of water is introduced into the reaction zone, the amount of water being such that the molar ratio of water based on the starting alcohol is from 1:0.01 to 1:1.

8. A process as claimed in claim 1 wherein the reactants are fed to the reaction zone at a liquid hourly space velocity of from 0.1 to 5 $hr^{-1}$.

9. A process for producing an o-alkylated phenol comprising reacting a phenol compound of the formula:

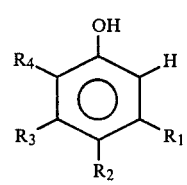

where $R_1$, $R_2$, $R_3$ and $R_4$ stand for hydrogen, alkyl radicals of 1 to 4 carbon atoms, or unsubstituted or substituted phenyl radicals, with a saturated aliphatic alcohol in the presence of a catalyst at a temperature of from 300° to 500° C., the molar ratio of said phenol compound to said alcohol ranging from 1:1 to 1:14, said catalyst comprising manganese oxide, silicon oxide, and at least one alkali metal compound, the atomic ratio of Mn:Si:alkali metal in said catalyst being 100:0.01–20:10$^{-5}$–5.

10. A process for producing an o-alkylated phenol comprising reacting a phenol compound of the formula:

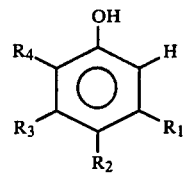

where $R_1$, $R_2$, $R_3$ and $R_4$ stand for hydrogen, alkyl radicals of 1 to 4 carbon atoms, or unsubstituted or substituted phenyl radicals, with a saturated aliphatic alcohol of from 300° to 500° C., the molar ratio of said phenol compound to said alcohol ranging from 1:1 to 1:14, said catalyst comprising manganese oxide, silicon oxide, at least one alkaline earth metal oxide, and at least one alkali metal compound, the atomic ratio of Mn:Si:alkaline earth metal:alkali metal in said catalyst being 100:0.01–20:0.01–30:10$^{-5}$–5.

11. A process as claimed in claim 1, 9 or 10 wherein said reaction is conducted in the presence of an inert gas.

12. A process as claimed in claim 9 or 10 wherein said alcohol is methyl alcohol or ethyl alcohol.

* * * * *